(12) United States Patent
Mielnik et al.

(10) Patent No.: US 7,265,253 B2
(45) Date of Patent: Sep. 4, 2007

(54) DECONTAMINATION OF CRITICAL MAIL

(75) Inventors: Thaddeus J. Mielnik, Concord, OH (US); David A. Karle, Girard, PA (US); Alex D. Biggie, Madison, OH (US); William John Thomas Biebesheimer, Perry, OH (US); Peter A. Burke, Skillman, NJ (US); Gerald E. McDonnell, Basingstoke (GB); Chad Rhodes, Lake Villa, IL (US); Elaine M. Kopis, St. Louis, MO (US)

(73) Assignee: Steris Inc., Temecula, CA (US)

( * ) Notice: Subject to any disclaimer, the term of this patent is extended or adjusted under 35 U.S.C. 154(b) by 652 days.

(21) Appl. No.: 10/280,950

(22) Filed: Oct. 25, 2002

(65) Prior Publication Data

US 2003/0138344 A1    Jul. 24, 2003

Related U.S. Application Data (60) Provisional application No. 60/351,676, filed on Oct. 25, 2001, provisional application No. 60/401,715, filed on Aug. 7, 2002.

(51) Int. Cl.
*A62D 3/00* (2006.01)
(52) U.S. Cl. ...................................... 588/299
(58) Field of Classification Search ................ 599/299, 599/313, 318, 320, 400, 401, 249.5; 588/299, 588/313, 318, 320, 400, 249.5
See application file for complete search history.

(56) References Cited

U.S. PATENT DOCUMENTS

| | | | | |
|---|---|---|---|---|
| 2,072,845 A | | 4/1937 | Gross et al. ................... 167/39 |
| 4,230,663 A | * | 10/1980 | Forstrom et al. ............. 422/33 |
| 4,454,605 A | * | 6/1984 | DeLucia ....................... 378/57 |
| 6,363,800 B1 | | 4/2002 | Call et al. ................. 73/863.22 |
| 6,887,710 B2 | * | 5/2005 | Call et al. ..................... 436/53 |
| 2002/0124664 A1 | | 9/2002 | Call et al. | |
| 2002/0150500 A1 | | 10/2002 | Carman et al. | |

FOREIGN PATENT DOCUMENTS

WO    WO99/32162    7/1999

OTHER PUBLICATIONS

Rice, "Ozone and Anthrax—Knowns and Unknowns", Ozone Science & Engineering vol. 24, pp. 151-158, 2002, XP001147252.

\* cited by examiner

*Primary Examiner*—Edward M. Johnson
(74) *Attorney, Agent, or Firm*—Fay Sharpe LLP (57) ABSTRACT

Mail which may be contaminated with a biotoxin, such as Anthrax, is received in a preliminary sorting area (16) including a dirty side sorting room (40) that is sealed to the ambient environment. The mail is loaded into a pass-through decontamination system (22) in which the mail is sterilized or otherwise decontaminated. The mail is removed from the pass-through system in a second or clean room (18) which is isolated from the first. The mail is then sorted and processed in the lean room (18). In the event that the sorting room (40) becomes contaminated or is suspected of being contaminated by pathogenic biological or chemical agents, a spray system (86) supplies a decontamination gas into the preliminary sorting area (16) to decontaminate the dirty side sorting room (40), any equipment (42, 44) in the room, and any mail located in the room.

23 Claims, 5 Drawing Sheets

DECONTAMINATION OF CRITICAL MAIL

This application claims the priority of U.S. Provisional Application Ser. No. 60/351,676, filed Oct. 25, 2001, and U.S. Provisional Application Ser. No. 60/401,715, filed Aug. 7, 2002.

BACKGROUND OF THE INVENTION

The present invention relates to the decontamination of sorting rooms, such as mailrooms, where there exists a possibility that biological or chemical contaminants may be introduced to the sorting room along with the items being sorted. It finds particular application in combination with a two-part decontamination system in which the mail items are subjected to a systematic high level decontamination process, while the sorting room and equipment therein are decontaminated periodically or intermittently, such as when a biological or chemical hazard is detected or suspected. It will be appreciated that the invention also finds utility in other applications and with other sterilization and decontamination techniques.

Mail sorting facilities, at corporations that are potential terrorist threats or which handle large volumes of mail, face the concern that a letter or package containing a hazardous material, such as a pathogenic bacteria or chemical agent, could enter the facility along with the regular mail. It has been found that mail sorting equipment is capable of releasing spores of *Bacillus anthracis*, the causative agent of anthrax, contained in sealed envelopes into the environment. The airborne spores contaminate other mail and also the sorting equipment, posing hazards both to workers in the sorting room and to mail recipients.

The spores tend to travel beyond the original mail sorting room into other parts of the facility, such as through air ducts, doors, and windows, risking contamination to large areas of the facility. A single contaminated letter is capable of infecting an entire facility. This results in a considerable loss in time while remediation is effected, in addition to the risks posed to workers in the facility.

The present invention provides a new and improved system and method of treatment of mail handling facilities which overcome the above-referenced problems and others.

SUMMARY OF THE INVENTION

In accordance with one aspect of the present invention, a method for handling mail is provided. The method includes receiving the mail in a preliminary sorting area, treating at least a portion of the mail with an antimicrobial gas, and, in the event that the preliminary sorting area is contaminated or suspected of being contaminated with a pathogenic biological or chemical agent, supplying a decontaminating gas to the preliminary sorting area to decontaminate the sorting area and equipment and mail located within the preliminary sorting area.

In accordance with another aspect of the present invention, a method of decontaminating incoming mail is provided. The method includes receiving potentially contaminated mail in a first room that is sealed to the ambient environment and loading the mail into a pass through sterilizer from the first room. The mail is decontaminated in the sterilizer. From a second room isolated from the first room, the mail is removed from the sterilizer. After the mail is removed from the sterilizer in the second room, the mail is sorted and processed.

In accordance with another aspect of the present invention, a system for handling mail is provided. The system includes a facility which is capable of being isolated from the surrounding environment. The facility includes an enclosure for receiving potentially contaminated incoming mail and a clean area, isolated from the enclosure, in which decontaminated mail is sorted for distribution. A decontamination system which receives and decontaminates the potentially contaminated mail is connected with the enclosure to receive the potentially contaminated mail therefrom and with the clean area to supply the decontaminated mail thereto.

In accordance with another aspect of the present invention, a system for handling potentially contaminated mail is provided. The system includes a dirty-side room in which the potentially contaminated mail is prepared for decontamination.

A decontamination system is connected with the dirty-side room for bulk decontamination of the potentially contaminated mail.

A source of decontaminant gas is connected with the dirty-side room for intermittently treating the dirty-side room for pathogenic biological or chemical agents.

One advantage of at least one embodiment of the present invention is that it reduces the hazards posed by potentially contaminated mail.

Another advantage of at least one embodiment of the present invention is that mail handling equipment and mail are separately and effectively decontaminated.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 1 is a schematic view of a mail handling facility in accordance with the present invention.

FIG. 2 is a perspective view of a mobile mail handling facility;

FIG. 3 is a plot showing pressure changes throughout a vapor hydrogen peroxide decontamination cycle;

FIG. 4 is a perspective rendering of a mail handling facility in accordance with the present invention;

FIG. 5 is a perspective rendering of a second embodiment of a mail handling facility in accordance with the present invention.

DETAILED DESCRIPTION OF THE PREFERRED EMBODIMENTS

With reference to FIGS. 1 and 2, a mail handling facility 10 is shown. Items to be sorted, such as packages, letters, and other items of mail enter the facility from a loading dock 12 via an air lock 14 and undergo a preliminary sorting, are examined if appropriate, and distributed to different locations for different treatment. The facility provides for both routine decontamination of mail, even where no specific biological or chemical hazard has been identified, and for intermittent decontamination of the facility when a specific hazard risk has been identified.

The facility includes a "dirty side" 16, where all incoming mail items are treated as being potentially contaminated with a biological or chemical pathogenic agent, such as anthrax, small pox, LSD, nerve gas or the like, and a "clean side" 18, where the items are processed without concern for contamination, having been subjected to a decontamination process. The clean side 18 is separated from the dirty side 16 by a pathogenic agent impermeable barrier 20, such as a wall. Between the dirty side 16 and the clean side 18, the items pass through a pass-through decontamination system 22, designed to destroy any potential pathogenic agents which may be associated with the items. The decontamination system 22 may be a single sterilizer or more than one sterilizer.

Biological pathogenic agents, as used herein means microorganisms, such as bacterial spores, vegetative bacteria, viruses, molds, and fungi capable of killing or causing severe injury to mammals, particularly humans. Included among these are viruses, such as equine encephalomyelitis and smallpox; bacteria, such as those which cause plague (*Yersina pestis*), anthrax (*Bacillus anthracis*), and tularemia (*Francisella tularensis*); and fungi, such as *coccidioidomycosis*; as well as toxic products expressed by such microorganisms; for example, the botulism toxin expressed by the common *Clostridium botulinium* bacterium.

Chemical pathogenic agents include poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to injure, disable or kill mammals and which can be degraded or otherwise rendered harmless by a process which includes oxidation. Exemplary chemical pathogenic agents include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl) sulfide (mustard gas or "HD") and dichloro(2-chlorovinyl)arsine (commonly known as Lewisite); nerve agents, such as ethyl-N, N dimethyl phosphoramino cyanidate (commonly known as Tabun or agent GA), o-ethyl-S-(2-diisopropyl aminoethyl) methyl phosphono-thiolate (commonly known as agent VX), isopropyl methyl phosphonofluoridate (commonly known as Sarin or Agent GB), methylphosphonofluoridic acid 1,2,2-trimethylpropyl ester (commonly known as Soman or Agent GD). Chemical pathogens also includes substances which temporarily or permanently disable people or mammals.

The term "chemical pathogenic agent" includes substantially pure chemical compounds, but the term also contemplates mixtures of agents in any proportions, as well as those agents in impure states. "Chemical pathogenic agents," as used herein, also includes partially or completely degraded chemical pathogenic agents, e.g., gelled, polymerized, or otherwise partially or totally decomposed chemical warfare agents.

The decontamination system 22 is designed to handle a regular throughput of incoming mail, such as is received daily in a mail sorting facility for a large company or government body. The decontamination system may be designed to handle all mail entering the facility, or mail may be sorted into classes, and only certain classes of mail subjected to decontamination. Alternatively, different decontamination systems are employed for different classes of mail. For example, remittance mail may be treated with a form of radiation effective for destroying microorganisms, such as electron beam radiation (produced by an electron accelerator) or gamma radiation, while other mail is decontaminated with ethylene oxide. Ionizing radiation, particularly of short wavelength, such as gamma and e-beam radiation, destroys microorganisms by breaking chemical bonds in biologically important molecules such as DNA, and by creating free radicals and reactive molecules which chemically attack the organism.

In an alternative embodiment, ionizing radiation is used for decontamination of all types of mail, including remittance mail and mail classed as critical.

In yet another embodiment, a multi-component vapor, such as hydrogen peroxide, is used for decontamination of all or part of the mail.

Figure 2:
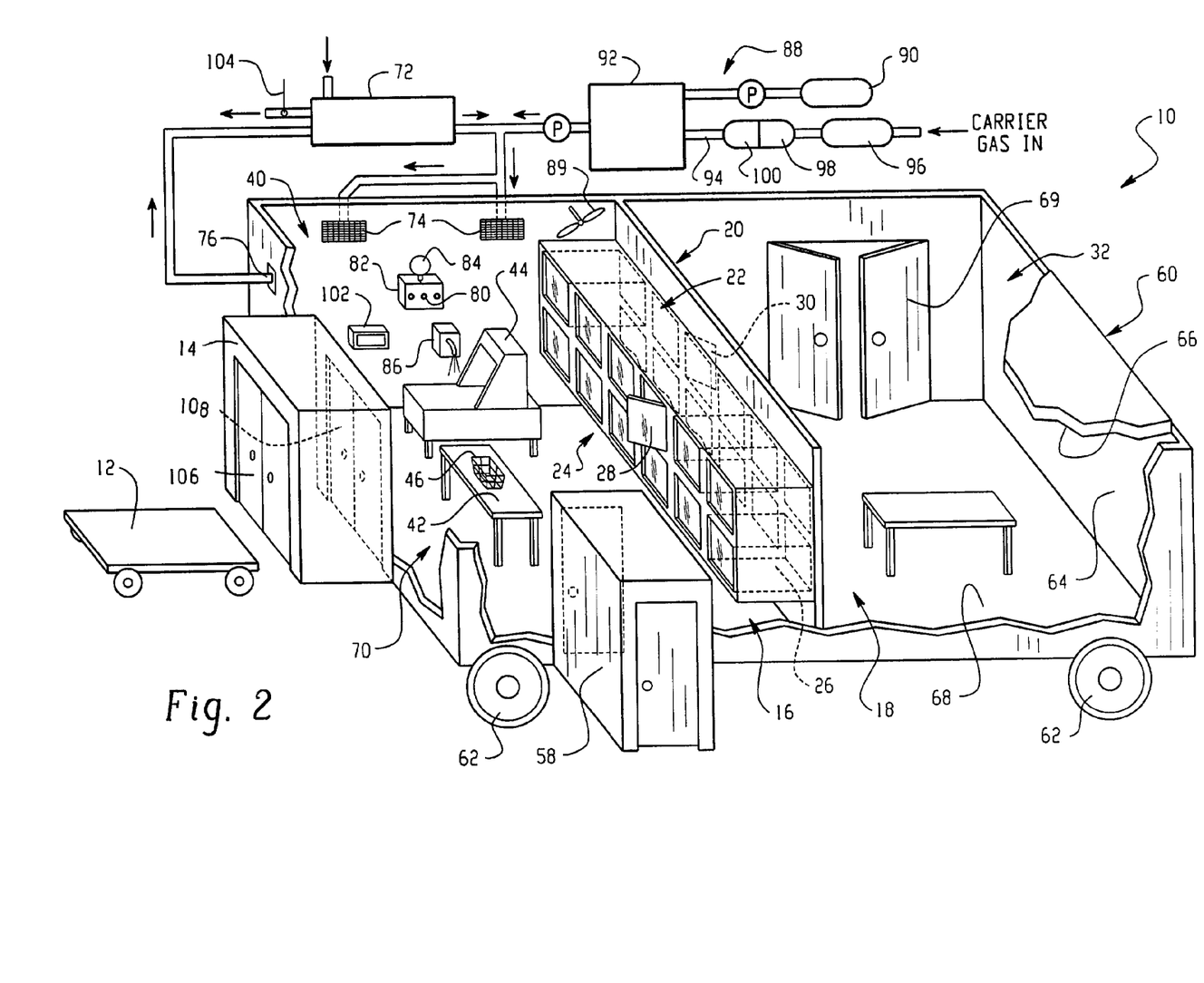

Ethylene oxide is a particularly preferred oxidant for regular treatment of incoming mail. It has good materials compatibility, being safe for use with paper, CDs, electronic storage media, video disks, and the like. A preferred decontamination system 22 includes a bank 24 of ethylene oxide sterilizers, each with a sterilization chamber 26. Interlocking doors 28, 30 are provided on the clean and dirty sides of each chamber 26, the dirty side door 28 remaining locked when the clean side door 30 is opened, and vice versa. Specifically, each chamber 26 has its own entrance door 28, on the dirty side, through which potentially contaminated items are loaded into the sterilization chamber 26. Each chamber also has an exit door 30 on the clean side 18, through which decontaminated items are removed from the chamber into a clean room 32, where further sorting and distribution takes place. As illustrated in FIG. 2, the decontamination system 22 forms part of the wall 20, with the dirty side entrance doors 28 on one side of the wall and the clean side exit doors 30 on the other side of the wall. The clean side 18 is thus isolated from the dirty side 14 of the facility.

The ethylene oxide sterilizers 26 may be analogous to those found in hospitals for treating contaminated medical instruments, as described, for example, in U.S. Pat. No. 4,241,010. One such suitable sterilizer is an Eagle 3017 sterilizer obtainable from STERIS Corp. having interlocking double doors and a chamber size of about 5 cu. ft. A bank 24 of 8-12 such sterilizers is capable of handling about 50,000 pieces of mail a day. It is preferable to use a number of small sterilizers (i.e., less than about 10 cu.ft. chamber size), rather than a larger sterilizer, since the hazards posed by the quantities of ethylene oxide in much larger chambers generally demand the use of blended gas at higher pressures.

Prior to sterilization, the chamber 26 is evacuated to a pressure of about 60-90 torr, or less. Several vacuum pulses are preferably employed to improve removal of air trapped in the items. Ethylene oxide from a cartridge or bulk supply (not shown) is then fed to the chamber 26 to bring the chamber to an above-atmospheric pressure, such as about 8 psig. During the sterilization phase, the chamber is preferably warmed, for example to about 55° C. The time taken for decontamination depends on the several factors, such as the volume and density of mail items, and the level of assurance desired. For high levels of assurance, e.g., about $10^{-8}$ (no more than 1 in $10^8$ pathogenic species remaining after decontamination), a decontamination time of about 1-4 hours is preferred, most preferably, about 2 hrs.

The chamber 26 is then evacuated and/or aerated to remove residual ethylene oxide from the chamber and items being decontaminated. Ethylene oxide diffuses slowly from "hard" polymers, such as acrylic and amide polymers, polyvinylchloride, and from kraft paper and glassine paper. Thus, a combination of vacuum and aeration is preferably used to speed removal of the residual ethylene oxide. For some items, such as those made from leather, diffusion is so slow that it is preferable to avoid ethylene oxide treatment of these items. One or more aeration cycles may be used in which air is admitted to the chamber and then removed by vacuum, to ensure that ethylene oxide which has absorbed into the items is removed. Typically, the aeration/evacuation portion of the cycle is longer than the decontamination portion, to ensure that ethylene oxide concentration in the, mail is below an acceptably safe level. For example, the aeration portion of the cycle may be about 5-20 hrs, preferably about 10-15 hours. The total time between loading the items through the dirty side doors and unloading the decontaminated items via the clean side doors 30 is thus about 15 hours.

Figure 4:
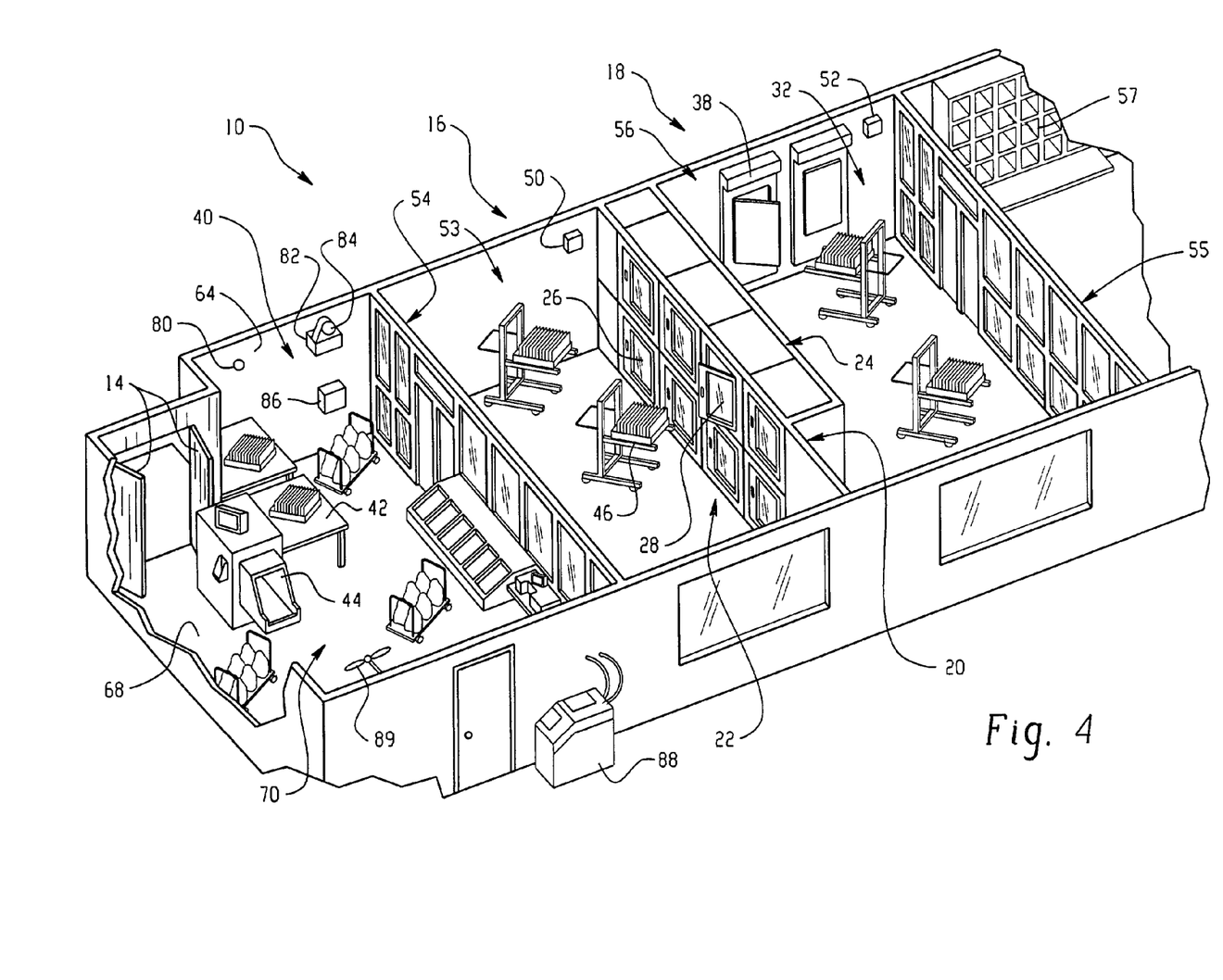

Optionally, or additionally, a separate aerator 38 (FIG. 4) is used for final aeration of the processed items, leaving the sterilizer chamber 26 free to handle another batch of unprocessed mail. Other sterilization systems, such as electron ($e^-$) beam sterilizers, can also separate the clean and dirty sides.

The dirty side 16 includes an enclosure, such as a preliminary sorting area or mail handling room 40, which houses the preliminary sorting equipment, such as sorting tables 42 and an x-ray scanner 44. The x-ray scanner 44 is used to examine suspicious packages, or all packages of above a certain size, to determine the contents. Items which are determined to pose a potential threat during or after sorting, or which contain items which are not readily handled by the decontamination system, such as food items, leather, and foil packages, are separated out and disposed of or subjected to special treatment in a separate isolation area. Other mail is sorted at the sorting tables into classes which axe to be pathogenically decontaminated or which are deemed safe to be distributed without pathogenic decontamination. Mail which is to be pathogenically decontaminated is loaded into receptacles, such as wire baskets or totes 46, of a suitable size to be loaded into the decontamination system 26.

Ethylene oxide monitors 50,52, such as Eagle EtO monitors available from STERIS Corp., are used in both the clean side 18 and dirty side 16 regions to ensure that workers are not subjected to ethylene oxide levels above a safe level in the event of a leakage. An area 53 adjacent the bank of sterilizers 26 is optionally separated from the rest of the sorting area by a plexiglass or glass wall 54 to minimize potential risks of ethylene oxide exposure. A second plexiglass or glass wall 55 isolates a sterilizer unloading region 56 of the clean room from an existing or conventional mail handling or sorting area 57 of the clean room.

Workers enter and leave the sorting room 40 through a changing room 58, where they suit up in appropriate protective garments to protect them against potential hazards. For example, microbe impermeable suits, boots, gloves, hats and face masks are worn. In the event of a determined or suspected contamination of the sorting room 40 by a pathogenic agent, workers exit the sorting room into the changing room 58 where they remove potentially contaminated clothing and wash in decontaminating cleansers. Suitable cleansers include those sold under the trade names CAL-STAT™, ALCARE™, and ALCARE PLUS™, available from STERIS Corp., which can be used with or without a water wash. Workers may be quarantined in an area of the changing room until they can be given appropriate medical attention if the suspected pathogenic contamination is determined to be particularly hazardous or contagious.

The dirty side 16 (preliminary sorting room 40 and sterilizer loading area 53) is isolated from other areas of the site or building in which it is housed. The sorting room, decontamination system 22, and optionally also the clean room 32 conveniently form a modular unit 60 which is transported, e.g., by a truck, to a site where mail handling is to take place. The modular unit 60 optionally has its own wheels 62 (FIG. 2), allowing it to be maneuvered around a site or between sites. The modular unit may be parked outside a facility to reduce the risk of cross-contamination still further. Interior walls 64, a ceiling 66, and a floor 68 of the unit 60 define the sorting room 40 and optionally also the clean room 32, or a portion thereof. The clean side optionally has doors 69, which connect to the loading dock or mail receiving door of an existing sorting facility.

The modular unit 60 is designed to maintain an airtight space 70 within the dirty side (particularly sorting room 40 and preferably also sterilizer loading area 53), where pathogenic contamination can be treated without risk of contamination to the clean room 32, or other areas of the site. Accordingly, the room 40 has its own independent air handling system 72, such as a heating, ventilating, and air conditioning (HVAC) system, for supplying air to the room 40 and for treating outgoing air from the room. The air is recycled at a high frequency, such as ten changes per hour, to minimize the chance that workers will be exposed to airborne contaminants. The room 40 preferably operates under a slight sub-atmospheric pressure, such that air tends to be sucked into the room 40, rather than leaving through doors and small openings. The HVAC system 72 has several inlets 74 and outlets 76, spaced throughout the room 40, through which purified incoming air enters the sorting room 40 and used air exits the sorting room. For facilities where large volumes of mail are to be handled, it is preferable to add additional modules 60, each one isolated from the others, so that if one of the modules' preliminary sorting rooms 40 is contaminated, the remaining modules 60 are able to continue with mail handling operations.

Within the sorting room 40, sensors 80 detect the presence of pathogenic agents. Preferably several sensors are provided which detect for different agents. Additionally, several sets of the sensors may be positioned at different locations within the room. U.S. Pat. No. 6,391,624, for example, describes a sensor capable of detecting anthrax and other clostridium and bacillus bacteria. The sensors 80 are hooked up to a central control system 82, which signals an alarm 84, such as a flashing light and/or audible alarm, in the event that one or more sensors 80 detects a pathogenic agent at a level above a predetermined threshold level. It is to be appreciated that many pathogenic organisms and chemicals are not readily detected by currently available sensors. Accordingly, the control system 82 has a manual component which relies on worker input in the event that a suspected release of a pathogenic agent has occurred. For example, workers may detect a smell, observe the release of a fine powder from a package, feel nauseous, or suffer other symptoms which they have been trained to associate with the potential release of a pathogenic agent. The alarm 84 may be actuated by a worker who determines that there is a risk of exposure to a suspected pathogenic agent.

The activation of the alarm 84 is a signal to the workers in the sorting room 40 that they should evacuate the sorting room and enter the changing area 58. Workers dressed in full biological hazard attire may enter the sorting room and apply a decontaminant spray to a suspicious package or letter. Alternatively, automated spray systems 86 are operated from outside the sorting room to direct a spray or fog over suspected contaminated items. For example, the spray systems 86 may release a liquid spray, fog or mist of an antimicrobial, antiviral, and sporicidal chemical known to be effective against a broad spectrum of known pathogenic agents. One suitable chemical for use as a spray is a liquid mixture of hydrogen peroxide and peracetic acid, which is effective at destroying biological pathogens on surfaces it contacts. Such a composition exhibiting broad spectrum activity is available from STERIS Corp. under the trade name SPOR-KLENZ. This liquid composition is capable of decontaminating contaminated mail in about fifteen to twenty minutes. It is safe for use with a variety of surfaces, including stainless steel, plastics, glass, floors, and walls.

Once the control system 82 detects that all workers have been evacuated from the sorting room, e.g., by using motion sensors (not shown), the room is sealed by closing and locking the doors 14. Air vents, if any, which are open to the atmosphere or to clean areas of the facility are closed. A decontamination of the entire sorting room 40 is then carried out with a room decontamination system 88 to ensure that pathogenic agents are destroyed or otherwise rendered harmless. The decontamination is preferably carried out with a gaseous oxidizing agent, such as hydrogen peroxide in vapor form. Hydrogen peroxide vapor has been shown to be effective against a variety of known biological and chemical pathogenic agents, such as hard to destroy spores of *Bacillus stearothermophilus, Bacillus anthracis*, smallpox virus, and the like. It is also effective at or close to room temperature (e.g., 15-30° C.), making it suitable for decontamination of large enclosures, such as rooms. Hydrogen peroxide vapor has a good material compatibility, rendering it safe for use with a variety of equipment and materials, including electronic equipment, such as computers. It also degrades to water and oxygen over time.

To destroy harmful biological pathogens in air and on surfaces throughout the room 40, it has been found that a concentration of hydrogen peroxide of about 1-2 mg/L, or more at 25° C. is effective to decontaminate a room in about 6-8 hours, or less. Longer times may be used at lower concentrations, or shorter times at higher concentrations. The vapor is preferably in the "dry" state, i.e., below the saturation point of the vapor, which varies with temperature. This avoids droplets of the vapor condensing on items in the room, which both reduces the effectiveness of the vapor and increases the time needed to remove the residual hydrogen peroxide after the vapor decontamination cycle is complete. Keeping the vapor in the dry state also reduces the risk of damage to electronic components and other items susceptible to water damage.

Figure 3:
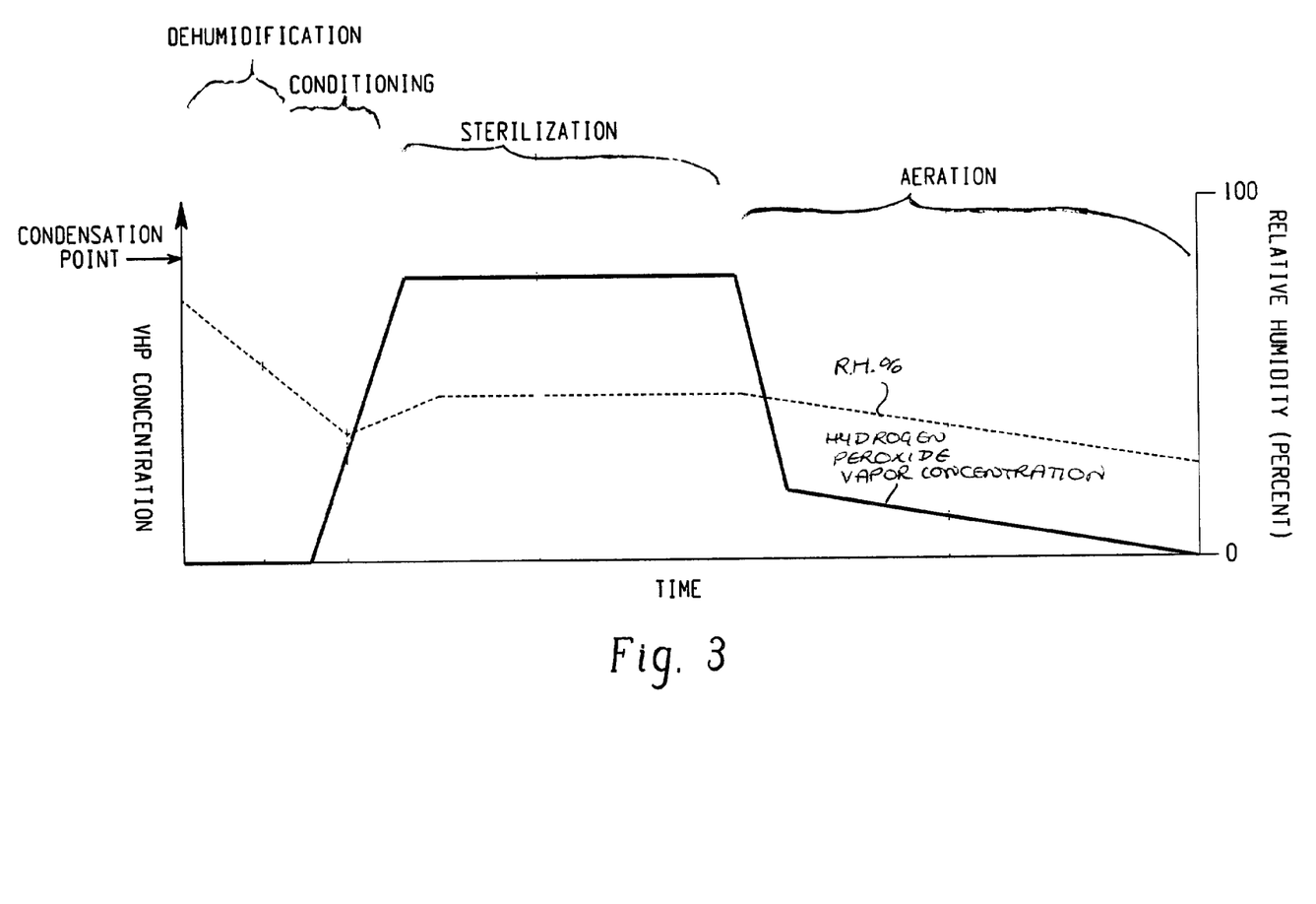

As shown in FIG. 3, a typical vapor hydrogen peroxide decontamination cycle consists of four phases: (1) dehumidification, where the room's HVAC system 72, or a separate dehumidifier, is used to reduce the level of moisture in the room, (2) conditioning, where the concentration of hydrogen peroxide is gradually increased by supplying hydrogen peroxide vapor to the room, (3) decontamination, where pathogenic biological agents are inactivated (often referred to as sterilization) and pathogenic chemical agents are oxidized to a form in which their pathogenic character is reduced or eliminated, and (4) aeration, where the HVAC system 72 is used to circulate fresh air into the room to reduce the hydrogen peroxide to safe levels (typically about 1 ppm, or less).

Preferably, the hydrogen peroxide is supplied to the sorting room 40 via the room's HVAC system 72. One suitable hydrogen peroxide decontamination system 88 suited to use with a HVAC system is a VHP® M1000 modular system, available from STERIS Corp. Alternatively, a separate unit 88 is used to supply the vapor to the room, through dedicated ductwork, such as a VHP® 1000, available from STERIS Corp. Such systems 88 are capable of sterilizing enclosures of up to 200,000 cu. ft. For larger enclosures, multiple hydrogen peroxide vapor generation systems 88 are used. Within the sorting room 40, fans 89 are activated to ensure distribution of the hydrogen peroxide, or other decontaminant vapor throughout the room.

The hydrogen peroxide vapor is readily formed from a solution of hydrogen peroxide in water, such as a 35% hydrogen peroxide solution, which is supplied from a reservoir 90, such as a tank, to a vapor generator 92. The generator 92 converts the liquid to a vapor, for example, by bringing droplets or a mist of the solution into contact with a heated plate or tube (not shown). Other gaseous oxidizing agents may be used, such as peracids, e.g., peracetic acid vapor, ozone, or chlorine gas, alone, or in combination with one or more gaseous oxidants including hydrogen peroxide vapor.

A carrier gas, such as air, is supplied to the vaporizer 92 via a carrier gas line 94 to mix with the liquid and/or vapor and carry the vapor out of the vaporizer 92. The carrier gas may be filtered by a filter 96, dehumidified by a dehumidifier 98, and optionally heated by a heater 100 before entering the vaporizer 92. The vapor and carrier gas mixture is fed into the ducts 78 of the HVAC system and carried along with the filtered air to the room inlets 74.

It will be appreciated that where vapor hydrogen peroxide is used in a decontamination system 22, in place of ethylene oxide, a vapor hydrogen peroxide generation system similar to the system 88 described above is optionally used to supply hydrogen peroxide vapor to the sterilization chamber 26.

One, or preferably several hydrogen peroxide sensors 102 in the sorting room 40 detect the level of hydrogen peroxide and/or water vapor in the sorting room to ensure that the hydrogen peroxide level in the room is maintained at a preselected level. The sensor 102 is connected with the control system 82, which adjusts the rate of introduction of hydrogen peroxide to the vaporizer, air flow rates, or the like, in response to detected hydrogen peroxide/water concentrations, to maintain the selected hydrogen peroxide concentration in the room 40. Suitable hydrogen peroxide sensors 102 are those which use infrared absorption by the vapor circulating in the room 40. The sensor preferably operates in a region of the infrared spectrum where water and/or hydrogen peroxide absorbs strongly, to provide a measure of the hydrogen peroxide concentration.

After the room sterilization phase is complete, the sensors 102 can be used to determine when the levels of hydrogen peroxide in the room 40 have dropped to a level at which it is safe for the workers to reenter. Additional hydrogen peroxide sensors 104 may be placed in the HVAC exhaust system ducts to check that hydrogen peroxide is not being released to the atmosphere at unsafe levels.

Figure 1:
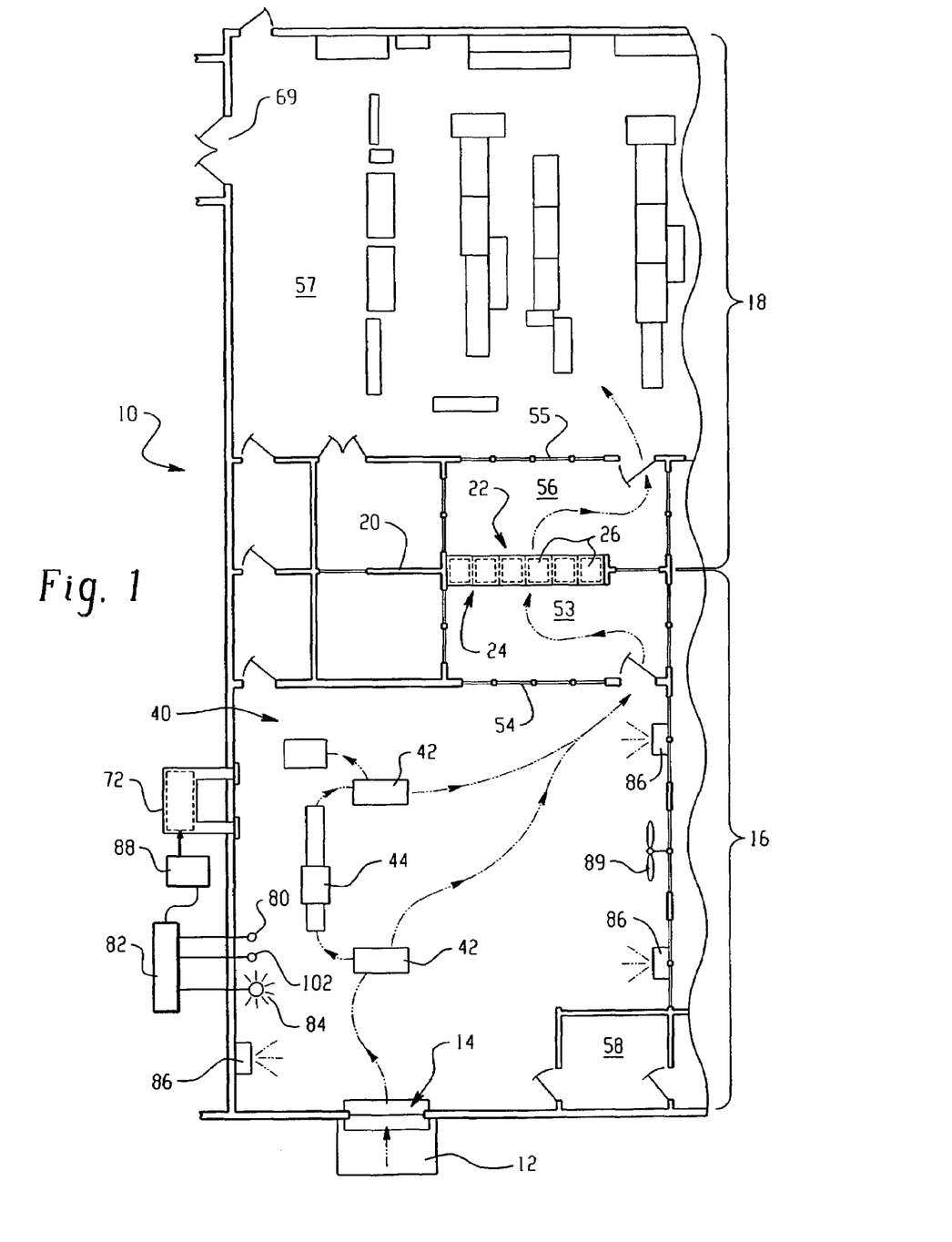
Figure 5:
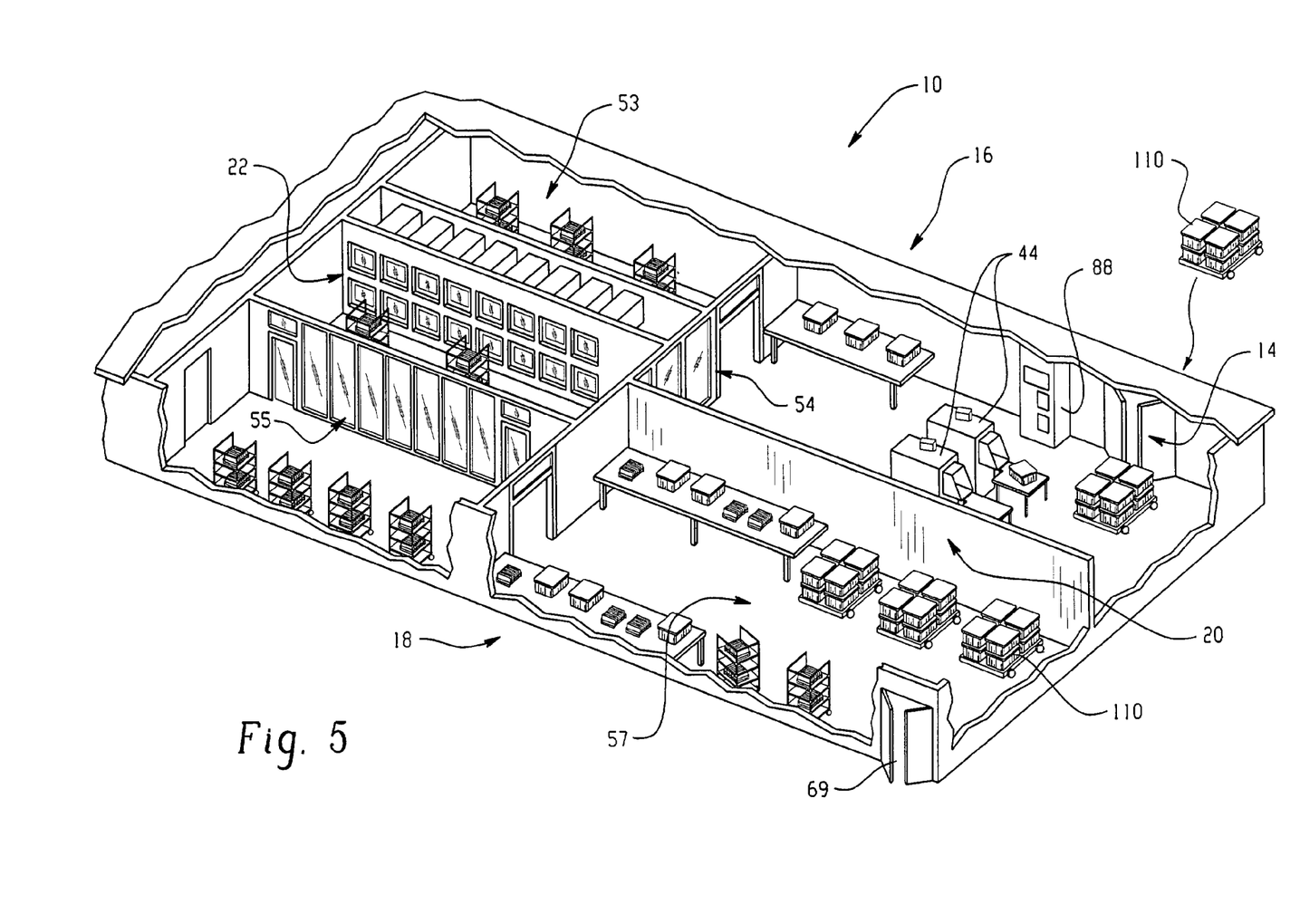

With reference now to FIG. 5, a mail handling facility 10, similar to that shown in FIGS. 1 and 2 is shown. The facility 10 is modular and operates as a self-contained unit, as for the facility of FIGS. 1 and 2. Items to be sorted, such as packages, letters, and other items of mail enter the facility from a loading dock via a door or airlock 14. Airlock 14 may take the form of an ante-room, providing space for handling incoming mail, with inner and outer doors 106, 108.

In this embodiment, the incoming mail is packaged, for example, at the Post Office or other sorting facility, in sealed containers, which are substantially impermeable to pathogens, such as air-tight plastic totes 110. Prior to bringing the totes in to the facility 10, e.g., in the air lock, workers, preferably in hazardous material handling suits, spray the exterior surfaces of the totes with a liquid spray, fog or mist of an antimicrobial, antiviral, and sporicidal chemical known to be effective against a broad spectrum of known pathogenic agents. One suitable chemical for use as a spray is SPOR-KLENZ. The totes are left outside the facility for a sufficient time to ensure that any microbial contaminants on the totes are destroyed. Such contaminants may have been picked up by the totes during handling at a central mail handling center or during transportation, for example, from having traveled in contaminated delivery trucks. For larger facilities, an automated spraying device, which treats the tote exteriors with the SPOR-KLENZ or other decontaminant spray, may be located in the airlock region.

Alternatively, or additionally, the interior of the delivery truck, and/or its contents may be pretreated with a sporicidal spray, hydrogen peroxide vapor or the like, to rid the mail truck of contaminants. This is particularly helpful when the same truck is used to transport the decontaminated mail to another site. Within the facility 10, the incoming mail is removed from the totes 110 before undergoing processing.

As with the embodiments of FIGS. 1 and 2, the mail undergoes a preliminary sorting in a "dirty side" 16, where all incoming mail items are treated as being potentially contaminated with a biological or chemical pathogenic agent before passing to a "clean side" 18, where the items are processed without concern for contamination, having been subjected to a decontamination process. A pathogenic agent impermeable barrier 20, such as a wall or walls separates the clean and dirty side. A pass-through decontamination system 22 microbially decontaminates the mail. The decontamination system 22 preferably includes a bank of ethylene oxide sterilizers or other microbial decontamination system (e.g., e-beam, gamma radiation, hydrogen peroxide vapor, or the like, as previously discussed) to destroy any potential pathogenic agents which may be associated with the items. After sorting, the decontaminated mail is repacked into totes 110, which have preferably been decontaminated, both inside and out. Particularly where the totes of processed mail are to be transported by truck or other vehicle, the totes are preferably air-tight to ensure that the processed mail does not become recontaminated by contact with contaminants in the truck. On reaching its final destination, each tote may be re-sprayed with a sporicidal agent to ensure that the mail does not become recontaminated during removal from the tote.

Alternatively, the totes 110 are packed in a microbe impermeable barrier, such as plastic or Tyvec™, which is removed from the totes at their final destination.

The pathogen treatment systems employed in the mail handling facility 10 can be extended to other areas of a mail delivery flowpath. Typically, mail enters the flowpath at a mailbox, from which pieces of mail are retrieved at regular intervals by postal workers. The mail is transported in sacks, cartons, or other handling devices to a local sorting hub. From the local sorting hub, the mail is transported to one or more distribution sorting hubs and is delivered to the recipients, such as the mail handling facility described above. At each step in the flowpath, there is a potential for contamination of workers or other mail due to the handling procedures. Hazard Analysis and Critical Control Point (HACCP) principles are used to assess the risks at each step and appropriate hazard prevention methods applied. These methods need not be applied at all times. However, preparations are preferably made in advance such that the hazard prevention techniques are implemented when the assessed risk suggests that they are necessary.

For example, postal workers are provided with a antimicrobial spray or dusting compound, such as SPOR-KLENZ™, which is applied to the contents of a mailbox before the postal worker retrieves the mail therefrom. The postal worker waits for a few minutes before opening the mailbox to allow the spray to destroy pathogenic agents on the surfaces of the mail. The postal worker is then assured that the mail can be handled without posing a health risk.

Local sorting hubs and distribution sorting hubs are optionally fitted with mail decontamination systems 22 as described above, e.g., ethylene oxide, gamma radiation, or e-beam sterilizers. Alternatively, all mail is sent to an offsite facility where it is passed through a mail decontamination system before returning to the hub for sorting. Room decontamination systems, such as the sorting room vapor hydrogen peroxide decontamination system described above, are optionally used at each of the hubs for decontamination of sorting rooms when a potential release of a pathogenic agent is detected. Other areas where contamination is possible are also fitted with area decontamination systems, such as offices, changing rooms, ventilation ducts, and the like. A single hydrogen peroxide vaporizer, for example, is capable of decontaminating a room or area of about 10,000 sq ft., or larger. For larger areas, multiple vaporizers are preferably employed. Hand and body washes, such as Alcare™, Alcare plus™, and Cal-Stat™ hand sanitizers, available from STERIS Corp., are provided for workers either for use as a preventative treatment or for use after handling potentially contaminated mail. Transportation vehicles, such as trucks, planes, and rail cars, are periodically decontaminated to remove pathogens, or decontaminated when a risk of decontamination is expected.

Mail handling devices, including cartons, totes, sacks, sorting equipment, x-ray equipment, and the like are also subjected to periodic or intermittent decontamination. For example, totes, cartons, or sacks are periodically or intermittently passed through a decontamination system, such as decontamination system 22, and/or sprayed with a sporicidal agent.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method for handling mail comprising:
   receiving the mail in a preliminary sorting area;
   treating at least a portion of the mail with an antimicrobial gas; and
   in response to the preliminary sorting area being contaminated or suspected of being contaminated with a pathogenic biological or chemical agent, supplying a decontaminating gas to the preliminary sorting area to decontaminate the sorting area and equipment and mail located within the preliminary sorting area.

2. The method of claim 1, wherein the antimicrobial gas includes ethylene oxide.

3. The method of claim 1, wherein the decontaminating gas includes hydrogen peroxide vapor 4. A method for handling mail comprising:
   receiving the mail in a preliminary sorting area;
   treating at least a portion of the mail with an antimicrobial gas;
   sensing a pathogenic biological or chemical agent in the sorting area with a sensor;
   the sensor signaling a control system of the presence of the agent; and the control system initiating a step of supplying a decontaminating gas to the preliminary sorting area in response to sensing a pathogenic agent above a predetermined acceptable level to decontaminate the sorting area and equipment and mail located within the preliminary sorting area.

5. The method of claim 1, wherein the decontaminating gas is supplied through a dedicated air handling system for the sorting area.

6. The method of claim 1, wherein the sorting area forms part of a modular unit, further including:
transporting the modular unit to a site where mail sorting and treating are to be carried out.

7. The method of claim 6, further including:
sorting the treated mail, the step of sorting being carried out in a clean region of the module which is isolated from the preliminary sorting area.

8. The method of claim 1, wherein the step of treating includes:
loading mail in a basket into a chamber of a sterilizer;
evacuating the sterilizer; and
introducing antimicrobial gas into the chamber, the mail being kept in the sterilizer for a sufficient time to decontaminate the mail.

9. The method of claim 8, further including, after the introducing step:
aerating the chamber to remove residual antimicrobial gas.

10. The method of claim 1, wherein the step of sorting includes:
separating the mail into mail which will be subjected to the treatment step, and mail which is unsuited to be treated in the treatment step.

11. The method of claim 1, further including, prior to the step of sorting:
transporting the mail to the sorting area in an airtight container; and
removing the mail from the airtight container.

12. The method of claim 11, further including, prior to the step of removing:
decontaminating an exterior surface of the container.

13. The method of claim 1, further including, after the step of treating:
transporting the treated mail in a container which is substantially impermeable to pathogens.

14. A method of decontaminating incoming mail comprising:
receiving potentially contaminated mail in a first room that is sealed to the ambient environment;
loading the mail into a pass through sterilizer from the first room;
decontaminating the mail in the sterilizer;
from a second room isolated from the first room, removing the mail from the sterilizer; and
after the mail is removed from the sterilizer in the second room, sorting and processing the mail.

15. The method of claim 14, further including:
with all workers removed from the first room, treating the first room with a decontaminating vapor.

16. The method of claim 15 further including:
monitoring the first room for contamination; and
in response to sensing contamination, setting off an alarm to cause workers to evacuate the first room and performing the treating step.

17. The method of claim 14, further including:
examining the mail in the first room with x-rays.

18. The method of claim 14 further including:
receiving the mail in sealed containers in an ante-room at an entrance to the first room; and
treating the exterior surfaces of the containers with a chemical decontaminant prior to loading the mail into the sterilizer.

19. The method of claim 14, further including:
after the mail is removed from the sterilizer in the second room, packaging the mail in sealed containers for transport to another facility.

20. The method of claim 1, wherein the antimicrobial gas is different from the decontaminating gas.

21. The method of claim 1, wherein after mail is received in the preliminary sorting area, batches of the mail are placed into a pass-through sterilizer, the mail being treated with the antimicrobial gas in the pass-through sterilizer;
after treating the mail with the antimicrobial gas, removing the treated mail from the pass-through sterilizer from a mail sorting area, the preliminary sorting area being isolated from the mail sorting area to prevent a pathogenic biological or chemical agent from passing from the preliminary sorting area to the mail sorting area.

22. The method of claim 4 further including:
in response to sensing a pathogenic biological or chemical agent in the sorting area, triggering an alarm to signal workers in the sorting area to leave the sorting area and go to a changing room;
removing potentially contaminated clothing and washing in decontaminating cleansers.

23. A method for handling mail comprising:
passing sealed containers of mail through an air lock into a preliminary sorting room which is sealed to the ambient environment;
treating exterior surfaces of the containers with a chemical decontaminant;
removing the mail from the containers and placing the mail in a pass-through sterilizer;
decontaminating the mail in the pass-through sterilizer;
from a clean room which is separated from the preliminary sorting area
by a pathogenic agent impermeable barrier, removing the mail from the pass-through sterilizer;
monitoring the preliminary sorting room for the presence of an airborne pathogenic biological or chemical agent;
in response to sensing a pathogenic biological or chemical agent in the preliminary sorting room, evacuating workers from the preliminary sorting room and treating the preliminary sorting room with a decontaminating gas.

* * * * *